US012766954B2

(12) United States Patent
Jeon et al.

(10) Patent No.: US 12,766,954 B2
(45) Date of Patent: Oct. 20, 2026

(54) ALCOHOL SENSING SYSTEM AND METHOD FOR CONTROLLING THE SAME

(71) Applicants: Hyundai Motor Company, Seoul (KR); Kia Corporation, Seoul (KR); Hyundai Mobis Co., Ltd., Seoul (KR)

(72) Inventors: Seul Ki Jeon, Hwaseong-si (KR); Eung Hwan Kim, Seoul (KR); Yu Jin Jung, Seoul (KR); Yeon Su Kim, Gunpo-si (KR); Chang Won Lee, Seoul (KR)

(73) Assignees: Hyundai Motor Company, Seoul (KR); Kia Corporation, Seoul (KR); Hyundai Mobis Co., Ltd., Seoul (KR)

( * ) Notice: Subject to any disclaimer, the term of this patent is extended or adjusted under 35 U.S.C. 154(b) by 728 days.

(21) Appl. No.: 17/979,096

(22) Filed: Nov. 2, 2022

(65) Prior Publication Data

US 2023/0173917 A1 Jun. 8, 2023

(30) Foreign Application Priority Data

Dec. 8, 2021 (KR) ........................ 10-2021-0174901

(51) Int. Cl.
*B60W 40/08* (2012.01)
*B60K 28/06* (2006.01)
*G01N 33/497* (2006.01)

(52) U.S. Cl.
CPC ......... *B60K 28/06* (2013.01); *G01N 33/4972* (2013.01)

(58) Field of Classification Search
CPC .... B60K 28/06; B60K 28/063; B60K 28/066; G01N 33/4972; G01N 33/0047; B60W 2040/0836
USPC ............ 73/23.3, 31.01, 863, 863.01, 864.73; 340/603, 632–634; 600/529, 532, 543; 422/84, 85
See application file for complete search history.

(56) References Cited

U.S. PATENT DOCUMENTS

| | | | |
|---|---|---|---|
| 4,607,719 A | 8/1986 | Rugis et al. | |
| 7,911,350 B2 | 3/2011 | Shoji et al. | |
| 8,201,437 B2 | 6/2012 | Takata | |
| 8,441,357 B2 | 5/2013 | Ohya | |
| 2017/0274768 A1 | 9/2017 | Hök et al. | |
| 2022/0072469 A1 * | 3/2022 | Abizeid | ............. B01D 53/0407 |

FOREIGN PATENT DOCUMENTS

| | | | | |
|---|---|---|---|---|
| JP | 2010203904 A | 9/2010 | | |
| KR | 200344255 Y1 * | 3/2004 | ......... G01N 33/4972 | |
| KR | 20040023374 A | 3/2004 | | |
| KR | 20100026170 A | 3/2010 | | |
| KR | 20110133831 A | 12/2011 | | |
| KR | 101916026 B1 | 11/2018 | | |
| KR | 20180120834 A | 11/2018 | | |

* cited by examiner

*Primary Examiner* — Robert R Raevis
(74) *Attorney, Agent, or Firm* — Slater Matsil, LLP

(57) ABSTRACT

An embodiment alcohol sensing system includes an air duct including a first opening and a second opening, the first opening being opened to an outside of the air duct, and a sensor module connected to the air duct at the second opening, the sensor module including a fan configured to rotate in opposite directions and an alcohol sensor configured to measure an alcohol content in air.

2 Claims, 10 Drawing Sheets

ALCOHOL SENSING SYSTEM AND METHOD FOR CONTROLLING THE SAME

CROSS-REFERENCE TO RELATED APPLICATIONS

This application claims the benefit of Korean Patent Application No. 10-2021-0174901, filed on Dec. 8, 2021, which application is hereby incorporated herein by reference.

TECHNICAL FIELD

The present disclosure relates to an alcohol sensing system.

BACKGROUND

Many traffic accidents are often caused by drunk driving, so most countries prohibit drunk driving in order to prevent accidents caused by drunk driving. Typically, if the blood alcohol content exceeds a predetermined threshold, punishment is almost certain.

In order to prevent drunk driving from happening, it has been proposed to provide an alcohol sensing system in a vehicle to monitor the driver's condition (drunk-driving condition). For example, the alcohol sensing system includes an air intake tube having an inlet located in a cluster fascia, an alcohol sensor disposed in an outlet of the air intake tube, and a controller controlling the driving condition of the vehicle using an alcohol sensing value measured by the alcohol sensor.

In the alcohol sensing system according to the related art, however, the inlet of the air intake tube is fully opened to draw the driver's breath into the sensor. If water, beverage, and other foreign substances are drawn into the inlet of the air intake tube, the alcohol sensing system would malfunction.

The above information described in this background section is provided to assist in understanding the background of the inventive concept, and may include any technical concept which is not considered as the prior art that is already known to those skilled in the art.

SUMMARY

The present disclosure relates to an alcohol sensing system. Particular embodiments relate to an alcohol sensing system and a method for controlling the same that can minimize the occurrence of malfunctions due to moisture and other foreign substances.

Embodiments of the present disclosure can solve problems occurring in the prior art while advantages achieved by the prior art are maintained intact.

An embodiment of the present disclosure provides an alcohol sensing system and a method for controlling the same that can minimize the occurrence of malfunctions due to moisture and other foreign substances by preventing the inflow of moisture and other foreign substances or discharging them.

According to an embodiment of the present disclosure, an alcohol sensing system may include an air duct having a first opening and a second opening and a sensor module connected to the air duct. The first opening may be opened to the outside of the air duct, and the sensor module may be connected to the second opening. The sensor module may include a fan which is rotatable in opposite directions and an alcohol sensor which measures the alcohol content.

As the fan is rotatable in opposite directions, the air may be directed from the first opening of the air duct to the second opening of the air duct or from the second opening of the air duct to the first opening of the air duct. Accordingly, the alcohol sensing system may selectively operate in an alcohol sensing mode and a moisture removal mode.

The air duct may further include a filter detachably mounted in the first opening, and the filter may have a plurality of holes allowing only the air to pass therethrough.

The filter may filter moisture and other foreign substances, thereby blocking the moisture and other foreign substances from entering the air duct.

The air duct may further include a first holder provided on a top edge of the first opening and a second holder provided on a bottom edge of the first opening. The filter may include a first engaging portion detachably engaged with the first holder and a second engaging portion detachably engaged with the second holder.

The first holder may have a first recess extending in a longitudinal direction of the air duct, the second holder may have a second recess extending in a direction perpendicular to the longitudinal direction of the air duct, the first engaging portion may be detachably fitted into the first recess, and the second engaging portion may be detachably fitted into the second recess.

The first engaging portion and the second engaging portion of the filter may be perpendicular to each other, and the first holder and the second holder of the air duct may be perpendicular to each other. The first engaging portion and the second engaging portion of the filter may be detachably engaged with the first holder and the second holder of the air duct, respectively, so that the filter may be easily mounted and replaced.

The air duct may further include a grille mounted in the first opening, the grille may include a plurality of struts spaced apart from each other in a vertical direction, the plurality of struts may define a plurality of holes, and each strut may be inclined downwardly from the inside of the air duct to the outside of the air duct.

The plurality of struts may be inclined downwardly from the inside of the air duct to the outside of the air duct in the first opening. When the air together with moisture and other foreign substances is drawn into the air duct, the moisture and other foreign substances may move to the outside of the air duct along the inclined struts.

The air duct may further include a grille detachably mounted in the first opening and an inclined bottom wall adjacent to the first opening.

The grille may have a plurality of holes and a bottom discharge hole adjacent to a bottom end of the inclined bottom wall.

Accordingly, the moisture and other foreign substances present in the air duct may move along the inclined bottom wall and be discharged to the outside of the air duct through the bottom discharge hole.

The air duct may further include a flap mounted in the first opening to move between an open position and a closed position, and the flap may be rotated by a driving motor so that the first opening may be opened or closed.

When the flap is in the opening position, the first opening of the air duct may be opened so that the air in the passenger compartment may flow into the passage of the air duct, and the alcohol sensor may measure the alcohol content contained in the air including the driver's breath. When the flap is in the closed position, the first opening of the air duct may be closed so that the air, moisture, and other foreign substances in the passenger compartment may be prevented from flowing into the passage of the air duct.

The air duct may further include a drain hole provided in a bottom wall thereof.

Accordingly, the moisture present in the air duct may be discharged to the outside through the drain hole.

The air duct may further include a collection chamber provided around the drain hole and designed to collect moisture, and the collection chamber may be defined by a recessed wall which is recessed downwardly from the bottom wall of the air duct.

The recessed wall may have at least one inclined wall which is inclined toward the drain hole.

The air duct may further include an absorbing pad attached to the bottom of the drain hole, and the absorbing pad may be made of a material capable of absorbing moisture.

As the absorbing pad is attached to the bottom of the drain hole, the moisture discharged through the drain hole may be absorbed by the absorbing pad, thereby preventing the moisture from flowing down to other components.

The air duct may further include a humidity sensor provided therein, and the sensor module may further include a heater provided therein.

According to another embodiment of the present disclosure, a method for controlling the alcohol sensing system may include determining whether a humidity measured by the humidity sensor is higher than or equal to a threshold and rotating the fan in a first direction and stopping the heater when the measured humidity is lower than the threshold. The first direction may be a rotational direction of the fan in which the air is drawn from the outside of the air duct to the sensor module through the air duct.

The method may further include rotating the fan in a second direction and operating the heater when the measured humidity is higher than or equal to the threshold. The second direction may be a rotational direction of the fan in which the air is discharged from the sensor module to the outside of the air duct.

BRIEF DESCRIPTION OF THE DRAWINGS

The above and other objects, features and advantages of embodiments of the present disclosure will be more apparent from the following detailed description taken in conjunction with the accompanying drawings, in which.

DETAILED DESCRIPTION OF ILLUSTRATIVE EMBODIMENTS

Figure 1:
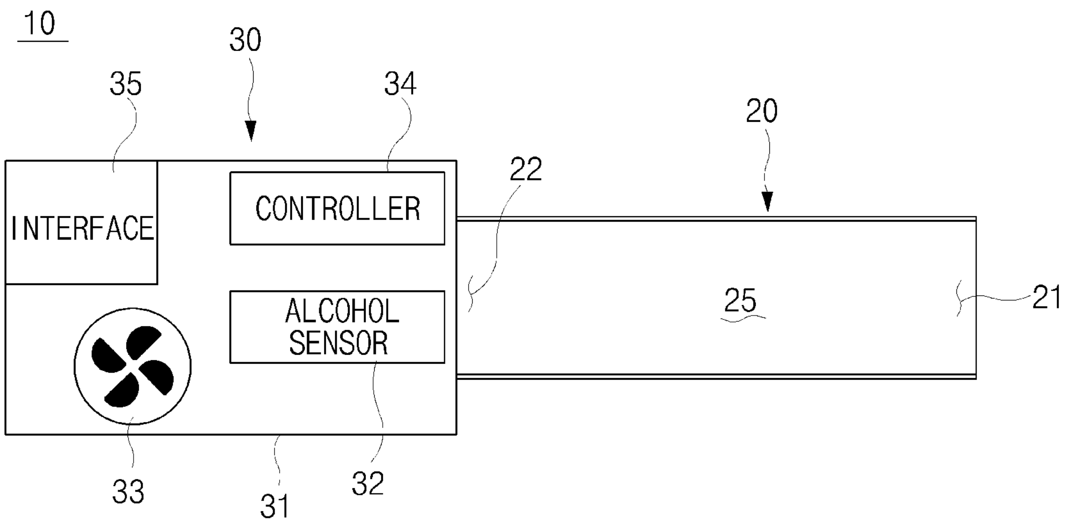
FIG. 1 illustrates an alcohol sensing system according to an exemplary embodiment of the present disclosure.

Hereinafter, exemplary embodiments of the present disclosure will be described in detail with reference to the accompanying drawings. In the drawings, the same reference numerals will be used throughout to designate the same or equivalent elements. In addition, a detailed description of well-known techniques associated with the present disclosure will be omitted in order not to unnecessarily obscure the gist of the present disclosure.

Terms such as first, second, A, B, (a), and (b) may be used to describe the elements in exemplary embodiments of the present disclosure. These terms are only used to distinguish one element from another element, and the intrinsic features, sequence or order, and the like of the corresponding elements are not limited by the terms. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted as having meanings equal to the contextual meanings in the relevant field of art, and are not to be interpreted as having ideal or excessively formal meanings unless clearly defined as having such in the present application.

Referring to FIG. 1, an alcohol sensing system 10 according to an exemplary embodiment of the present disclosure may include an air duct 20 and a sensor module 30 connected to the air duct 20.

The air duct 20 may include a first opening 21 and a second opening 22, and the air duct 20 may have a passage 25 defined therein. The first opening 21 may be opened to the outside of the air duct 20 (that is, a passenger compartment of the vehicle), and accordingly the driver's breath, air, and the like may be drawn into the passage 25 of the air duct 20 through the first opening 21. The second opening 22 may directly communicate with the sensor module 30. The air duct 20 may have various shapes and various lengths, and the air duct 20 may have a shape and a length that match those of a component in which the air duct is mounted.

The sensor module 30 may include a housing 31, an alcohol sensor 32 received in the housing 31, a fan 33 rotatably provided in the housing 31, a controller 34 controlling the operations of the alcohol sensor 32 and the fan 33, and an interface 35 connected to an interface of the vehicle.

The alcohol sensor 32 may be configured to measure the alcohol content contained in the air passing through the passage 25 of the air duct 20.

The fan 33 may be configured to be rotatable in opposite directions (a first direction and a second direction) by a bidirectional motor.

When the fan 33 rotates in the first direction, the air may flow from the first opening 21 of the air duct 20 to the second opening 22 of the air duct 20, and accordingly the air including the driver's breath in the passenger compartment may be drawn into the sensor module 3*o* through the passage 25 of the air duct 20. That is, the first direction may be a rotational direction of the fan 33 in which the air is forcibly drawn from the outside of the air duct 20 to the sensor module 30 through the passage 25 of the air duct 20.

When the fan 33 rotates in the second direction, the air may flow from the second opening 22 of the air duct 20 to the first opening 21 of the air duct 20, and accordingly moisture, foreign substances, and the like remaining in the sensor module 30 may be discharged to the passenger compartment through the first opening 21. That is, the second direction may be a rotational direction of the fan 33 in which the air, moisture, and other foreign substances are forcibly discharged from the sensor module 30 to the outside of the air duct 20 through the passage 25 of the air duct 20.

The alcohol sensing system 10 according to an exemplary embodiment of the present disclosure may selectively operate in an alcohol sensing mode and a moisture removal mode according to changes in the rotational direction of the fan 33. In the alcohol sensing mode, as the fan 33 rotates in the first direction, the air may be drawn into the sensor module 30 through the air duct 20, and the alcohol sensor 32 of the sensor module 30 may measure the alcohol content in the air. In the moisture removal mode, as the fan 33 rotates in the second direction, the air may be discharged from the sensor module 30 to the outside of the air duct 20 (that is, the passenger compartment) through the air duct 20, and accordingly moisture may be removed from the air duct 20 and the sensor module 30.

Figure 2:
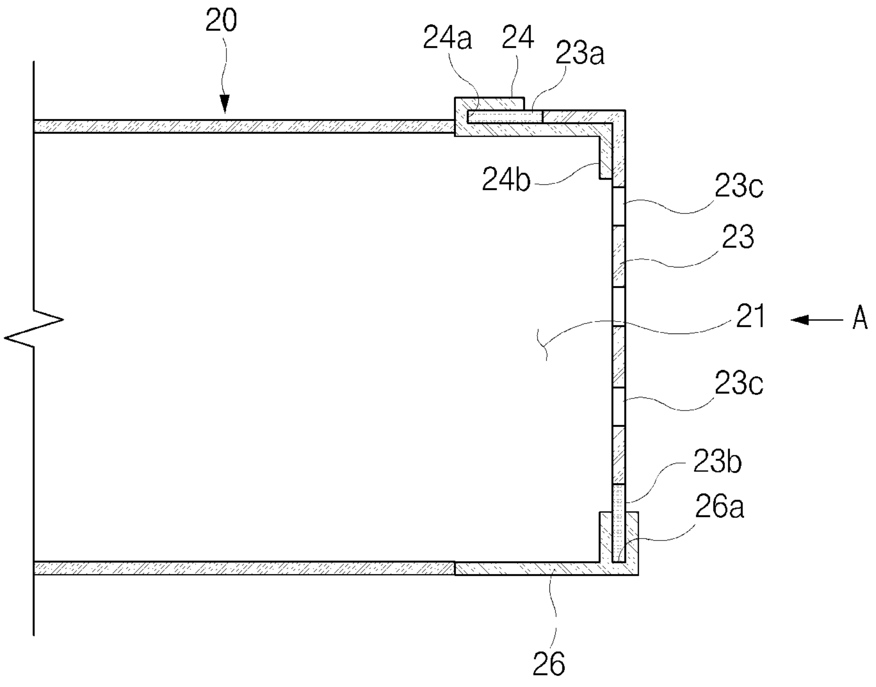
FIG. 2 illustrates a state in which a filter is mounted in a first opening of an air duct in an alcohol sensing system according to an exemplary embodiment of the present disclosure.
Figure 3:
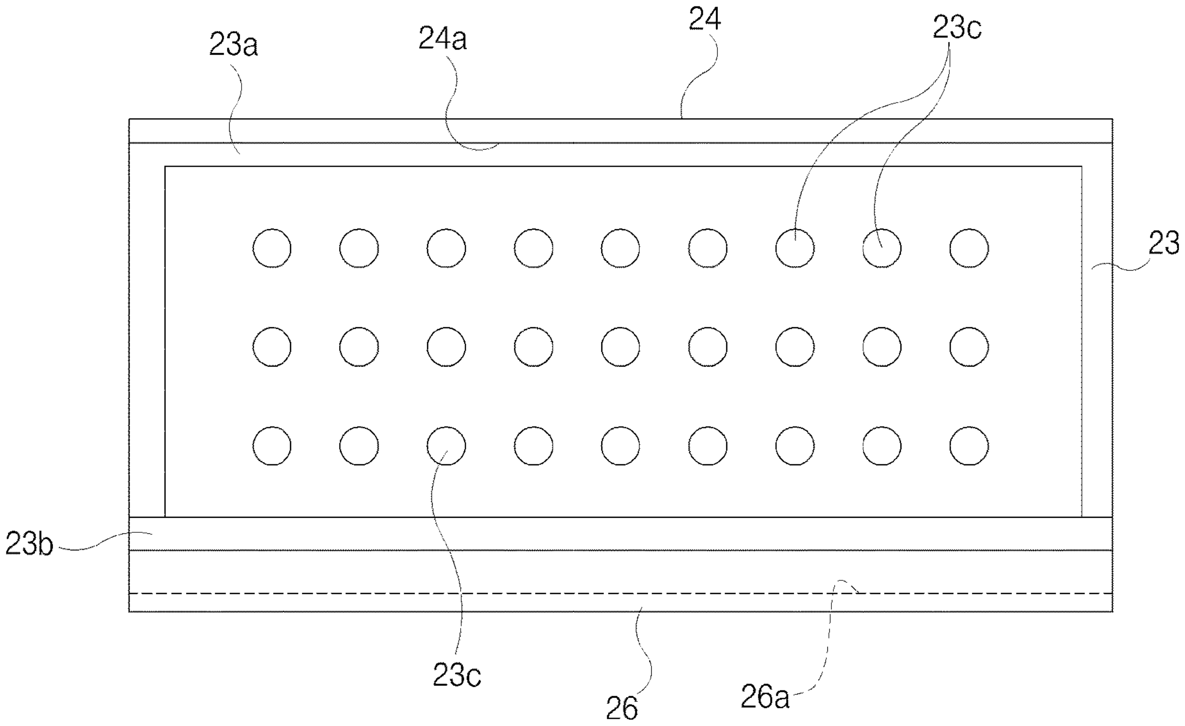
FIG. 3 illustrates a view, which is viewed in a direction indicated by arrow A of FIG. 2.

Referring to FIGS. 2 and 3, the air duct 20 may further include a filter 23 detachably mounted in the first opening 21, and the filter 23 may have a plane perpendicular to a longitudinal direction of the air duct 20. The filter 23 may filter moisture and other foreign substances, thereby blocking the moisture and other foreign substances from entering the passage 25 of the air duct 20. The filter 23 may be a mesh structure that prevents the inflow of moisture and/or other foreign substances. According to an exemplary embodiment, the filter 23 may have a plurality of holes 23*c*, and each hole 23*c* may have a size and a shape that allow only the air to pass therethrough and prevent moisture and/or solid materials from passing therethrough.

The air duct 20 may include a first holder 24 and a second holder 26 provided around the first opening 21. The first holder 24 may be disposed on a top edge of the first opening 21, and the first holder 24 may have a first recess 24*a*. The first recess 24*a* may extend in the longitudinal direction of the air duct 20, and the first recess 24*a* may have a U-shaped cross section that is horizontally opened to the outside of the air duct 20 (the passenger compartment). The first holder 24 may have a support shoulder 24*b* supporting the filter 23, and the support shoulder 24*b* may extend in a direction perpendicular to the longitudinal direction of the air duct 20. That is, the support shoulder 24*b* may extend in a direction parallel to the filter 23.

The second holder 26 may be disposed on a bottom edge of the first opening 21, and the second holder 26 may have a second recess 26*a*. The second recess 26*a* may extend in the direction perpendicular to the longitudinal direction of the air duct 20, and accordingly the second recess 26*a* may extend in a direction perpendicular to the first recess 24*a*. The second recess 26*a* may have a U-shaped cross section that is opened to the center of the first opening 21. That is, the second recess 26*a* may be opened upwardly.

The filter 23 may include a first engaging portion 23*a* detachably engaged with the first holder 24 and a second engaging portion 23*b* detachably engaged with the second holder 26. The first engaging portion 23*a* may be provided on a top end of the filter 23, and the first engaging portion 23*a* may extend in the longitudinal direction of the air duct 20. The first engaging portion 23*a* may have a shape and a size that match those of the first recess 24*a* of the first holder 24, and accordingly the first engaging portion 23*a* may be detachably fitted into the first recess 24*a* of the first holder 24. The second engaging portion 23*b* may be provided on a bottom end of the filter 23, and the second engaging portion 23*b* may extend in the direction perpendicular to the longitudinal direction of the air duct 20. The second engaging portion 23*b* may have a shape and a size that match those of the second recess 26*a* of the second holder 26, and accordingly the second engaging portion 23*b* may be detachably fitted into the second recess 26*a* of the second holder 26.

As described above, the first engaging portion 23*a* and the second engaging portion 23*b* of the filter 23 may be perpendicular to each other, and the first holder 24 and the second holder 26 of the air duct 20 may be perpendicular to each other. The first engaging portion 23*a* and the second engaging portion 23*b* of the filter 23 may be detachably engaged with the first holder 24 and the second holder 26 of the air duct 20, respectively, so that the filter may be easily mounted and replaced. That is, the mountability and replaceability of the filter may be improved.

Figure 4:
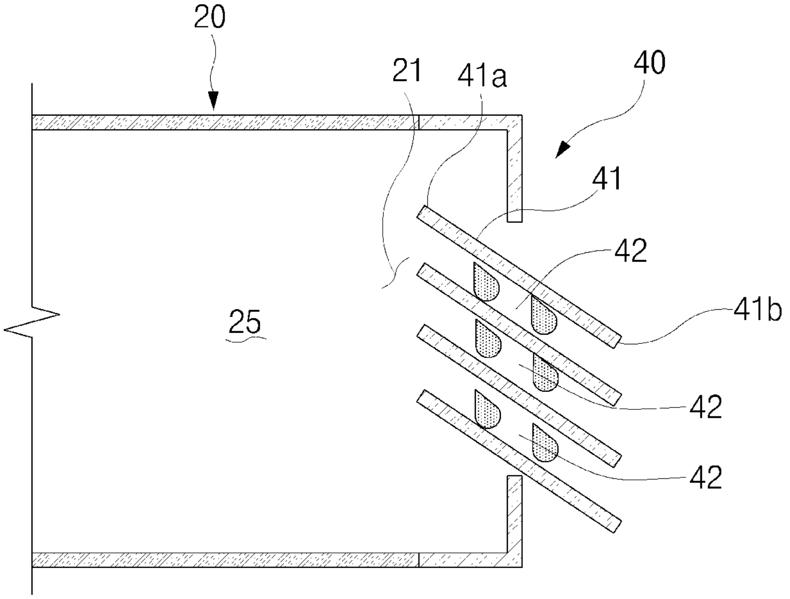
FIG. 4 illustrates a state in which a grille is mounted in a first opening of an air duct in an alcohol sensing system according to an exemplary embodiment of the present disclosure.

Referring to FIG. 4, the air duct 20 may further include a grille 40 detachably mounted in the first opening 21. The grille 40 may cover the first opening 21, and the grille 40 may have a plurality of holes 42 allowing the air to pass therethrough. The grille 40 may have a plurality of struts 41 spaced apart from each other in a vertical direction. The plurality of holes 42 may be defined by the plurality of struts 41, and the air may flow in/out of the air duct 20 through the plurality of holes 42.

Each strut 41 may be inclined downwardly from the passage 25 of the air duct 20 toward the passenger compartment. Specifically, the strut 41 may include a first end portion 41*a* located in the passage 25 of the air duct 20, and a second end portion 41*b* located in the outside of the air duct 20 (the passenger compartment). As the strut 41 is inclined downwardly from the passage 25 of the air duct 20 toward the outside of the air duct 20, the first end portion 41*a* may be located higher than the second end portion 41*b*. When the air together with moisture and other foreign substances is drawn into the air duct 20, the moisture and other foreign substances may move to the outside of the air duct 20 along the inclined struts 41, and accordingly the moisture and other foreign substances may be effectively prevented from entering the air duct 20.

Figure 5:
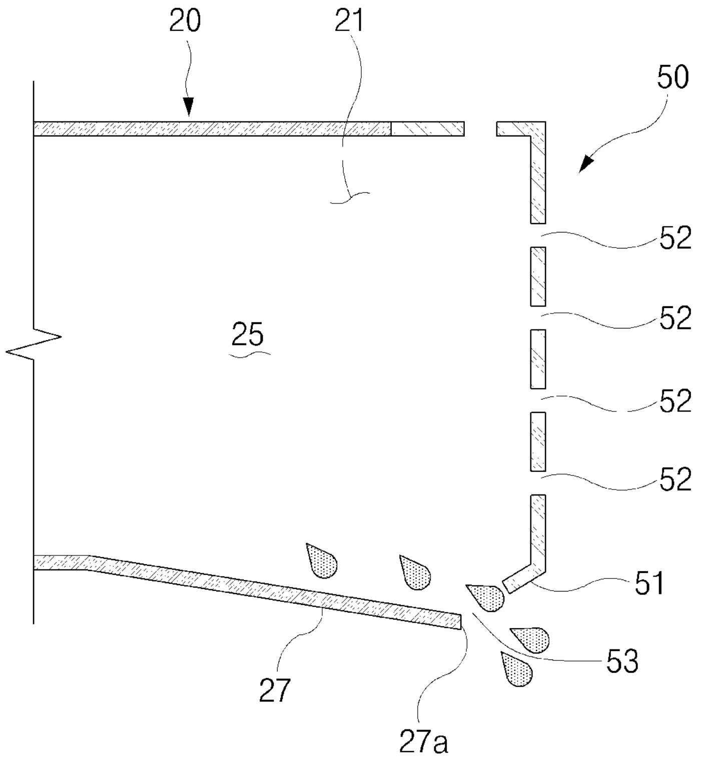
FIG. 5 illustrates a state in which a grille is mounted in a first opening of an air duct in an alcohol sensing system according to an exemplary embodiment of the present disclosure.

Referring to FIG. 5, the air duct 20 may further include a grille 50 detachably mounted in the first opening 21, and the grille 50 may have a plurality of holes 52 allowing the air to pass therethrough. The grille 50 may include an inclined bottom-end wall 51 provided on a bottom end thereof, and a bottom discharge hole 53 may be provided in the inclined bottom-end wall 51. A bottom wall of the air duct 20 may further include an inclined bottom wall 27 adjacent to the first opening 21, and the inclined bottom wall 27 of the air duct 20 may be inclined at an angle corresponding to that of the inclined bottom-end wall 51 of the grille 50. In particular, a bottom end 27*a* of the inclined bottom wall 27 may be adjacent to the bottom edge of the first opening 21 of the air duct 20, and accordingly the bottom end 27*a* of the inclined bottom wall 27 may be adjacent to the bottom discharge hole 53. Accordingly, the moisture and/or other foreign substances present in the passage 25 of the air duct 20 may move along the inclined bottom wall 27 and be discharged to the outside of the air duct 20 through the bottom discharge hole 53.

Figure 6:
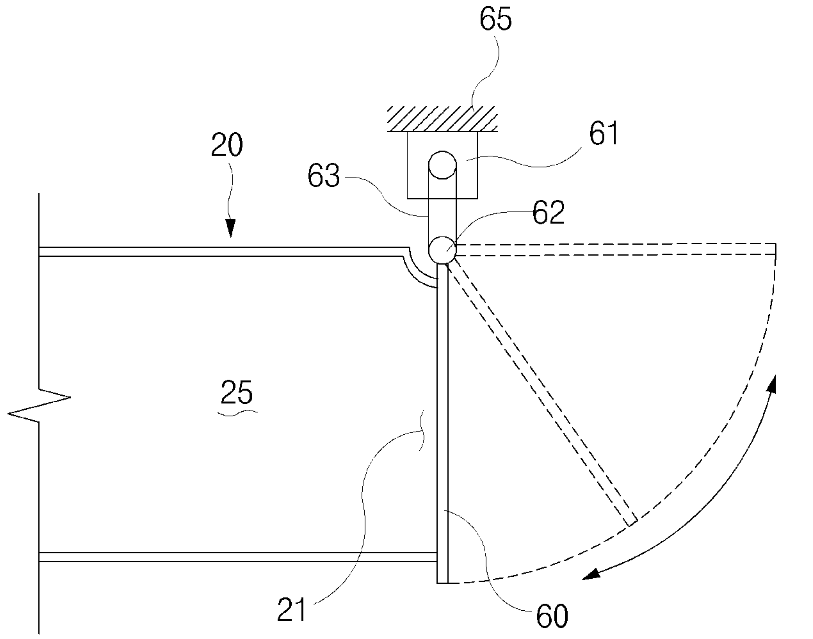
FIG. 6 illustrates a state in which a flap is mounted in a first opening of an air duct in an alcohol sensing system according to an exemplary embodiment of the present disclosure.

Referring to FIG. 6, the air duct 20 may further include a flap 60 which is mounted in the first opening 21 to move between an open position and a closed position. The flap 60 may be rotated by a driving motor 61. The flap 60 may include a pivot shaft 62 provided on a top end thereof, and the driving motor 61 may be connected to the pivot shaft 62 through a wire 63 or a belt. The driving motor 61 may be fixed to another component 65 adjacent to the alcohol sensing system 10. The flap 60 may be moved by the driving motor 61 between an open position and a closed position. When the flap 60 is in the open position, the first opening 21 of the air duct 20 may be opened so that the air in the passenger compartment may flow into the passage 25 of the air duct 20, and the alcohol sensor 32 may measure the alcohol content contained in the air including the driver's breath. When the flap 60 is in the closed position, the first opening 21 of the air duct 20 may be closed so that the air, moisture, and other foreign substances in the passenger compartment may be prevented from flowing into the passage 25 of the air duct 20.

Figure 7:
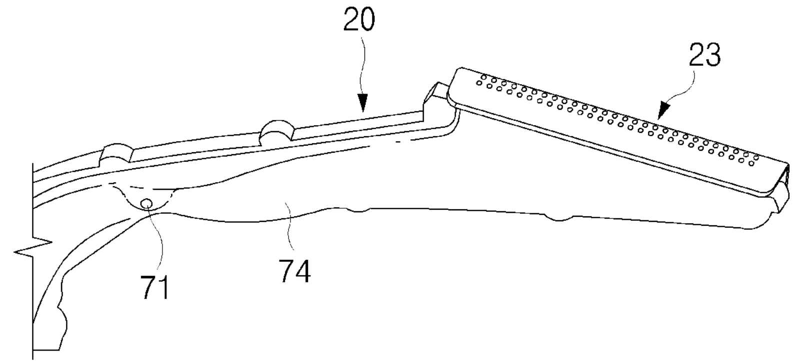
FIG. 7 illustrates a state in which a drain hole is provided in a bottom wall of an air duct in an alcohol sensing system according to an exemplary embodiment of the present disclosure.

Referring to FIG. 7, the air duct 20 may further include a drain hole 71 provided in the bottom wall thereof. The drain hole 71 may directly communicate with the passage 25 of the air duct 20. In particular, as the drain hole 71 is provided in a lowermost portion of the air duct 20, the moisture drawn into the air duct 20 may be discharged through the drain hole 71.

Figure 8:
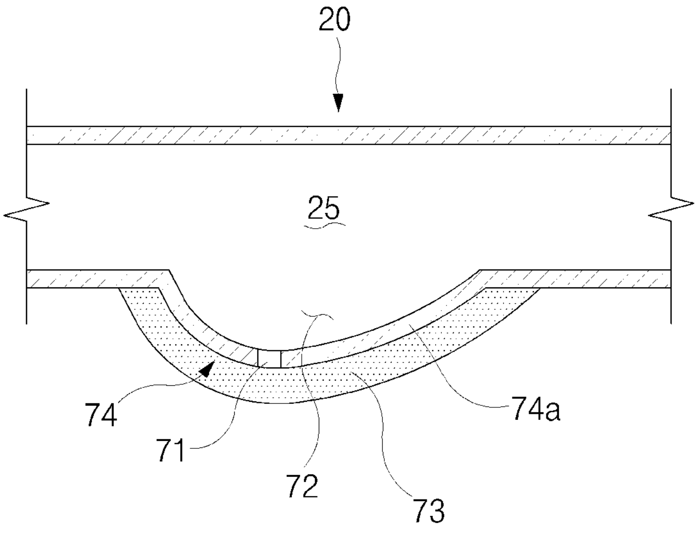
FIG. 8 illustrates a cross-sectional view of a portion of the air duct illustrated in FIG. 7.

Referring to FIG. 8, the air duct 20 may further include a collection chamber 72 provided around the drain hole 71, and the collection chamber 72 may be designed to collect moisture. The collection chamber 72 may be defined by a recessed wall 74 which is recessed downwardly from the bottom wall of the air duct 20. The recessed wall 74 may have at least one inclined wall 74*a* which is inclined toward the drain hole 71, and the moisture in the air duct 20 may be stably collected in the collection chamber 72 through the inclined wall 74*a*. The drain hole 71 may be provided in the bottom of the recessed wall 74. When the moisture is directly discharged to the outside of the air duct 20 through the drain hole 71, the moisture may fall to other components adjacent to the alcohol sensing system. To prevent this, the air duct 20 may further include an absorbing pad 73 attached to the drain hole 71 of the air duct 20. The absorbing pad 73 may be made of a material capable of absorbing moisture, such as a sponge. The absorbing pad 73 may be attached to a bottom surface of the recessed wall 74 to entirely cover the bottom surface of the recessed wall 74. In addition, the alcohol sensing system may be designed to have a layout in which other components may not be placed under the drain hole 71 of the air duct 20.

When water, a beverage, or the like flows into the passage 25 of the air duct 20 due to the driver's or occupant's mistake, or when moisture is collected in the passage of the air duct 20 due to low humidity in the passenger compartment, the moisture in the air duct 20 may be primarily discharged to the outside through the drain hole 71.

Figure 9:
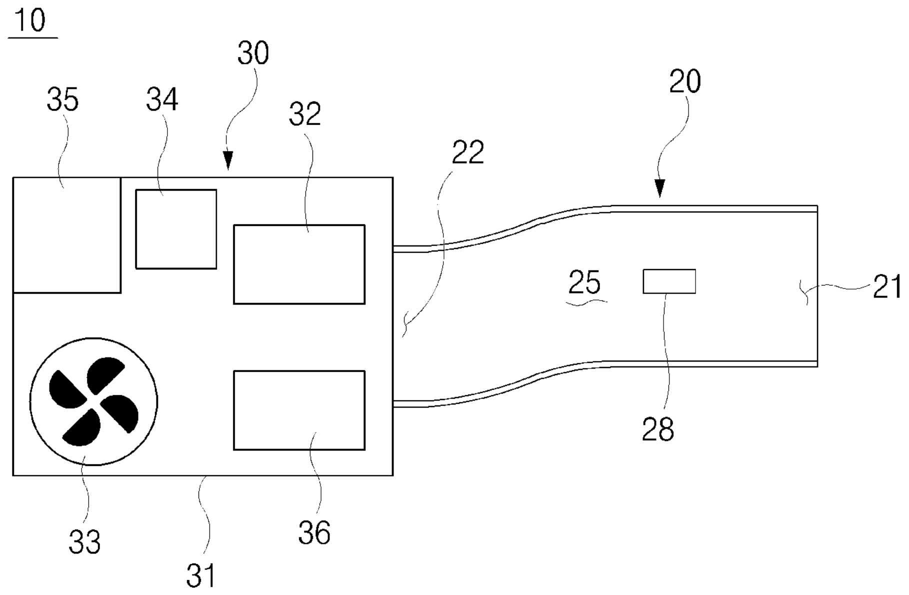
FIG. 9 illustrates an alcohol sensing system according to another exemplary embodiment of the present disclosure.

Referring to FIG. 9, the air duct 20 may further include a humidity sensor 28 disposed in the passage 25, and the sensor module 30 may further include a heater 36 received in the housing 31. The humidity sensor 28 may be electrically connected to the controller 34. The humidity sensor 28 may measure a humidity in the passage 25 of the air duct 20, and when the measured humidity is higher than or equal to a threshold, the controller 34 may operate the heater 36 and rotate the fan 33 in the second direction.

Before operating in the alcohol sensing mode in which the driver's condition (drunk-driving condition) is sensed, the alcohol sensing system 10 according to an exemplary embodiment of the present disclosure may operate in the moisture removal mode in which the moisture and other foreign substances in the air duct 20 are removed. For example, when a flow rate at which the driver's breath is drawn into the sensor module 30 through the air duct 20 is relatively insufficient or when the moisture collected in the passage of the air duct 20 is higher than or equal to a threshold, the controller 34 may rotate the fan 33 in the second direction and operate the heater 36 for a predetermined time, and accordingly the moisture in the air may be evaporated by heat generated by the heater 36, and the other foreign substances may be discharged to the outside through the first opening 21 of the air duct 20 (the moisture removal mode).

Figure 10:
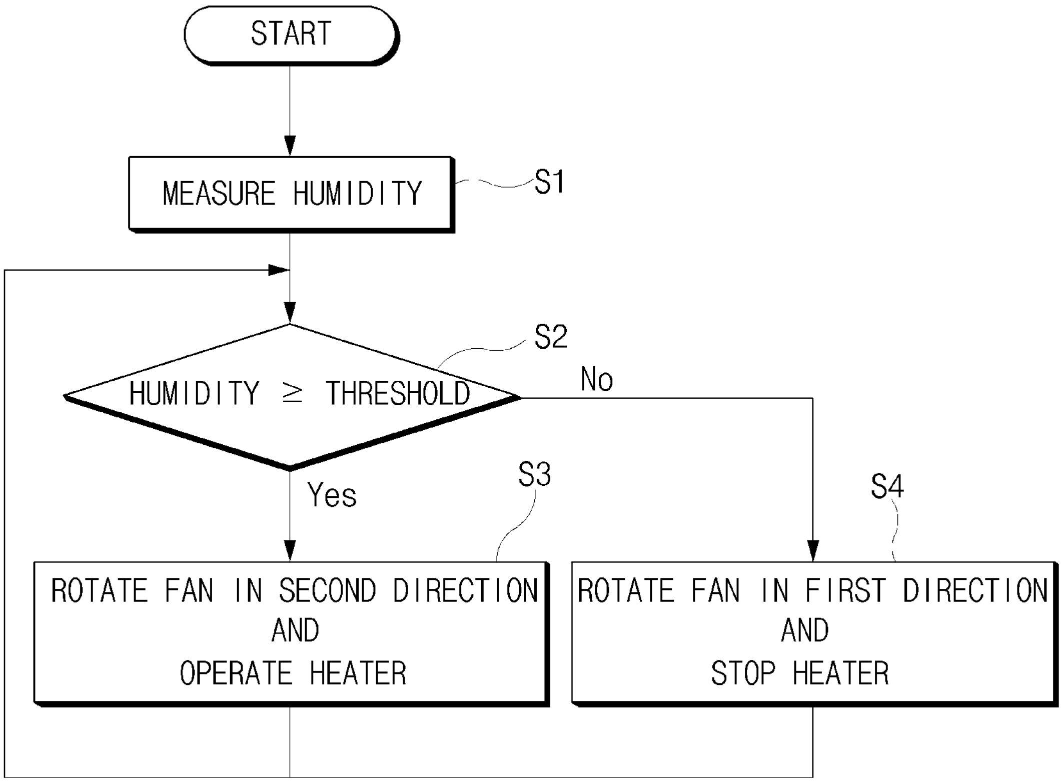
FIG. 10 illustrates a flowchart of a method for controlling an alcohol sensing system according to an exemplary embodiment of the present disclosure.

Referring to FIG. 10, when the vehicle is started (a start button is turned on), the humidity sensor 28 may automatically measure a humidity in the air duct 20 (S1). According to another exemplary embodiment, the driver or occupant may manually operate the humidity sensor 28 through a control panel, and accordingly the humidity sensor 28 may measure a humidity in the air duct 20.

The controller 34 may determine whether the measured humidity is higher than or equal to a threshold (S2). Here, the threshold may be the level of humidity that makes it difficult for the alcohol sensor 32 of the sensor module 30 to accurately measure the alcohol content in the air due to the humidity in the air duct 20.

When the humidity measured in S2 is higher than or equal to the threshold, the controller 34 may rotate the fan 33 in the second direction and operate the heater 36 (S3). Accordingly, the moisture may be evaporated by heat generated by the heater 36, and the other foreign substances may be discharged to the outside through the first opening 21 of the air duct 20 (the moisture removal mode).

When the humidity measured in S2 is lower than the threshold, the controller 34 may rotate the fan 33 in the first direction and stop the heater 36 (S4). Accordingly, the air may be drawn into the sensor module 30 through the passage 25 of the air duct 20, and the alcohol sensor 32 of the sensor module 30 may measure the alcohol content in the air (the alcohol sensing mode).

The alcohol sensing system 10 according to exemplary embodiments of the present disclosure may be disposed on various components in the passenger compartment of the vehicle. The alcohol sensing system 10 may be mounted on/in various components of the vehicle such as a cluster fascia, a steering column, a steering wheel, and a pillar. For example, when the alcohol sensing system 10 is mounted on the steering column, the first opening 21 of the air duct 20 may be located at a top end of the steering column, and the sensor module 30 may be located at a bottom end of the steering column. When the alcohol sensing system 10 is mounted in the cluster fascia, the first opening 21 of the air duct 20 may be located in the cluster fascia, and the sensor module 30 may be located on a cowl crossbar.

As set forth above, according to exemplary embodiments of the present disclosure, the sensor module may have the fan rotating in opposite directions so that the alcohol sensing system may selectively operate in the alcohol sensing mode and the moisture removal mode. By preventing the inflow of moisture and other foreign substances or discharging them, the occurrence of malfunctions due to the moisture and other foreign substances may be significantly reduced.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. An alcohol sensing system comprising:
an air duct comprising:
a first opening;
a second opening; and
a passage between the first opening and the second opening,
wherein the first opening is opened to an outside of the air duct;
a sensor device connected to the air duct at the second opening; and
a filter detachably mounted in the first opening, the filter comprising a plurality of holes to allow only air to pass therethrough,
wherein:
the air duct comprises a first holder provided on a top edge of the first opening and a second holder provided on a bottom edge of the first opening,
the filter comprises a first engaging portion detachably engaged with the first holder and a second engaging portion detachably engaged with the second holder,
the first holder comprises a first recess extending in a longitudinal direction of the air duct,
the second holder comprises a second recess extending in a direction perpendicular to the longitudinal direction of the air duct,
the first engaging portion is detachably fitted into the first recess, and
the second engaging portion is detachably fitted into the second recess.

2. A vehicle comprising:
a vehicle body; and
an alcohol sensing system mounted in an interior of the vehicle body, the alcohol sensing system comprising:
an air duct comprising:
a first opening;
a second opening; and
a passage between the first opening and the second opening,
wherein the first opening is opened to an outside of the air duct;
a sensor device connected to the air duct at the second opening; and
a filter detachably mounted in the first opening, the filter comprising a plurality of holes to allow only air to pass therethrough,
wherein:
the air duct comprises a first holder provided on a top edge of the first opening and a second holder provided on a bottom edge of the first opening,
the filter comprises a first engaging portion detachably engaged with the first holder and a second engaging portion detachably engaged with the second holder,
the first holder comprises a first recess extending in a longitudinal direction of the air duct,
the second holder comprises a second recess extending in a direction perpendicular to the longitudinal direction of the air duct,
the first engaging portion is detachably fitted into the first recess, and
the second engaging portion is detachably fitted into the second recess.

* * * * *